United States Patent [19]

Miller et al.

[11] Patent Number: 4,941,191
[45] Date of Patent: Jul. 10, 1990

[54] IMAGE ANALYSIS SYSTEM EMPLOYING FILTER LOOK-UP TABLES

[75] Inventors: John W. V. Miller, Toledo; Peter S. Miller, Perrysburg, both of Ohio

[73] Assignee: O-I Neg TV Products, Inc. Formerly known as Owens-Illinois Television Products, Inc.), Toledo, Ohio

[21] Appl. No.: 140,459

[22] Filed: Jan. 4, 1988

[51] Int. Cl.⁵ .................................................. G06K 9/52
[52] U.S. Cl. .......................................... 382/54; 382/8; 364/724.05; 364/724.19; 358/166; 358/106
[58] Field of Search ................. 382/54, 8; 364/724.05, 364/724.19; 358/166, 167, 106

[56] References Cited

U.S. PATENT DOCUMENTS

| | | | |
|---|---|---|---|
| 3,889,108 | 6/1975 | Cantrell | 364/724.19 |
| 4,489,390 | 12/1984 | Parenti et al. | 364/724.05 |
| 4,534,059 | 8/1985 | Yamada | 382/54 |
| 4,688,095 | 8/1987 | Beg et al. | 358/166 |
| 4,694,342 | 9/1987 | Klees | 382/54 |

Primary Examiner—Leo H. Boudreau
Assistant Examiner—Yon Jung

[57] ABSTRACT

An image processing system and filters applicable to such a system wherein digitized discrete signals, as pixel signals, are processed in a look-up table according to the sum of the current digitized value of a discrete signal multiplied by a factor and the digitized value of the signal from the look-up table for a preceding discrete signal multiplied by one less the factor for low pass filtering; and wherein high pass filtering is the difference between a factor times the current digitized value of a discrete signal and the digitized value of the low pass filter from the look-up table for a preceding discrete signal multiplied by a factor. Two dimensional filtering in a two dimensional array of pixels is afforded by identifying pixel signals by row and column and high pass filtering in pixel columns from row-to-row. Vector combinations of row and column filtered values are employed in a system for electro-optical inspection of the image of a product.

30 Claims, 4 Drawing Sheets

IMAGE ANALYSIS SYSTEM EMPLOYING FILTER LOOK-UP TABLES

This invention relates to a camera interface for general purpose front-end image analysis of signals scanned as by linear array cameras and more particularly for such analysis of standard scenes such as repetitive inspection of articles where anomalies in the scene represent the significant data to be analyzed.

Heretofore, electro-optical inspection systems have been utilized wherein a line scan camera views a band of discrete areas of an object and produces a series of pixel signals representing the light emanating from the discrete areas as corresponding pixel signals. Parallel and closely adjacent bands of discrete areas of the object can be viewed and produce a succession of series of pixel signals by various techniques including a camera with multiple lines of photoelectric signal source pixels for viewing the object, or by a camera with a single line of pixels moved relative to the object either by camera motion or object motion, wherein multiple scans of the linear array of pixels produces video signal sweeps.

In electro-optical inspection systems, the signal sweeps are monitored for significant signals, the anomalies representing defects or dimensional limits, and the data represented by the portion of the video signal for those pixels and pixel groups are processed to develop the inspection information. Differences in pixel signal level along a scan have been extracted and stored as one such form of data. Such differences can be derived by measurement of signals from pixel-to-pixel as absolute values or as relative values as logarithmically, or by measurement of individual pixel signal level deviations from a predetermined level or an average representing the general level of background light intensity of areas of the object adjacent the defective area.

Rapid scanning and processing to detect significant signals derived is necessary for high speed inspection systems employing line scan techniques so that the collected significant data can be processed as the inspection is performed.

According to one aspect of the present invention, the filtering of the signals to extract significant signals is performed digitally employing look-up tables. Such filtering can be two dimensional. That is, it can be along the scan direction, as from pixel-to-pixel in a scan, or transverse of the scan direction as between pixel-to-pixel in successive scans.

Signals indicative of significant anomalies in the corresponding areas of the object subject to inspection will be termed "events". Events are generated whenever the raw video or a filtered/log amplified version of the raw video crosses operator-selected thresholds. The camera signals to which thresholds are applied are first high-pass filtered in the scan direction and in the scan-to-scan direction. The high-pass filter algorithm, operating on each pixel signal, subtracts from its current value the low-passed filtered versions of the immediately preceding pixel series in both the scan or row direction and the scan-to-scan or column direction. The resulting row and column high-pass filter outputs are combined and applied to threshold patterns to generate events.

The filtering procedures permit reliable detection of intensity gradients having any direction on the object being inspected so as to be a general purpose front-end for image analysis. The video signal-data processing is adaptable to various optical systems of inspection including bright-field systems, wherein the defects appear as dark areas in a bright scene and the video signal portions from those pixels corresponding to the dark areas are of lower level than those for the general scene, dark-field systems, wherein the defects appear as bright areas in a dark scene and the video signal portions from those pixels corresponding to the bright areas are of a higher level than those for the general scene.

In some glassware inspection processes defects represented by a string of events may extend in only one direction and it may be desirable to suppress or ignore event strings extending in other directions. The algorithms employed for the low-pass filters, high-pass filters, and vector-combine sections of the system can be arranged to suppress the row or column signals or to emphasize one over the other as desired. These algorithms are utilized with operator selected constants in a central processing unit (CPU) connected to the system elements by a bus so that the look-up tables in RAMs employed in the filtering, vector-combining threshold definition and event processing sections produce results for all possible combinations of input signals by calculating those results and downloading them into the memories, RAMs, in the sections. Great flexibility is afforded in the system since the selection of constants and of the functions for the algorithms can be selected and combined over a wide range.

The pixel signals are generated by the camera in analog form. According to one aspect of the invention, anomalies in the image are enhanced by comparison of the camera signals with signals for a standard scene for the image of the object being analyzed. A pixel-by-pixel set of values for a standard scene is established in a memory by subjecting a defect-free standard object to the system analysis in a mode which enables the CPU to store digital signal values for each pixel from the standard image. This set of standard values, converted to analog form, is subtracted from the pixel values scanned during object analysis and the differences amplified to enhance the object anomalies. The analog signal levels of these anomalies are digitized to a finite number of levels and are processed as digital pixel signal levels in the filtering, vector-combining and event processing of the system.

The system offers the capability, where appropriate, to employ the high-pass filter detection of anomalies as the input into the event processing computer analysis, the difference signals of the scanned pixel signals from the predetermined standard signals for those pixels as the input into the computer for analysis, and combinations of the difference signals and high-pass filtered signals as the arrangement for event processing and computer analysis.

Controls are provided for selection of various operating modes whereby the data developed from signals derived along the row or scan direction of the pixel array and signals derived along a column of pixel signals for like pixel counts in successive scans of the pixel array are combined into a single digitized value termed a vector. Vector values are determined according to various functions of the row and column filtered signals. Such functions are applied through a CPU which pre-calculates values for all possible combinations of signal inputs and places them in a look-up table. Functions such as the sum of the absolute values of the inputs, the square root of the sum of the squares of the inputs, among others are appropriate for combining the row and column signals.

Threshold values for the vector values can be compared with the vector values and event signals developed. Masking of areas of the scene subject to analysis can be achieved in a control RAM which can operate on groups of pixel signals in row alignment and adjacent rows as super cells of such signals. Filter initialization can be utilized where appropriate as at the initial pixel in an effective scene or following a masked supercell.

The data selected for issuance to a CPU for analysis is stacked in a first-in-first-out memory. Economies in data storage are provided by employing signals in the stack for grouping pixel signal results as to categories such as initiation of the inspection of an object, and following each row scanned which contain anomalies classified as events.

The above and additional objects and features of this invention will be understood more readily from the following detailed description when read with reference to the accompanying drawings wherein.

The image processing system utilizing this invention operates on a bus 11 which controls operation of a camera 12 having a linear array of photosensitive cells, a linear array camera, or a two dimensional photosensitive array, a two-dimensional array camera. Camera 12 is adapted to receive light from discrete areas of the object 13 to be inspected on individual pixels and to develop a raw video signal by scanning of those pixels. In the case of a line scan camera, relative movement generally normal to the scan direction between the surface of the object 13 and the camera 12 coupled with successive scanning sweeps of the linear array develops a series of sweep signals representing light from discrete areas of the object aligned in the scanning direction in bands which are parallel and proximate for each successive sweep. Light on aligned proximate bands of the object can also be represented by successive sweeps of a two dimensional camera without the requirement of relative movement between camera and object between each scan. In the discussion which follows, a linear array camera and its operation will be discussed applied to an object circular in cross section having its axis which is normal to the cross section extend parallel to the linear array. That object is mounted for rotation about its axis to expose to the photocells or pixels of the array successive bands of discrete areas which are parallel to its axis.

Figure 1:
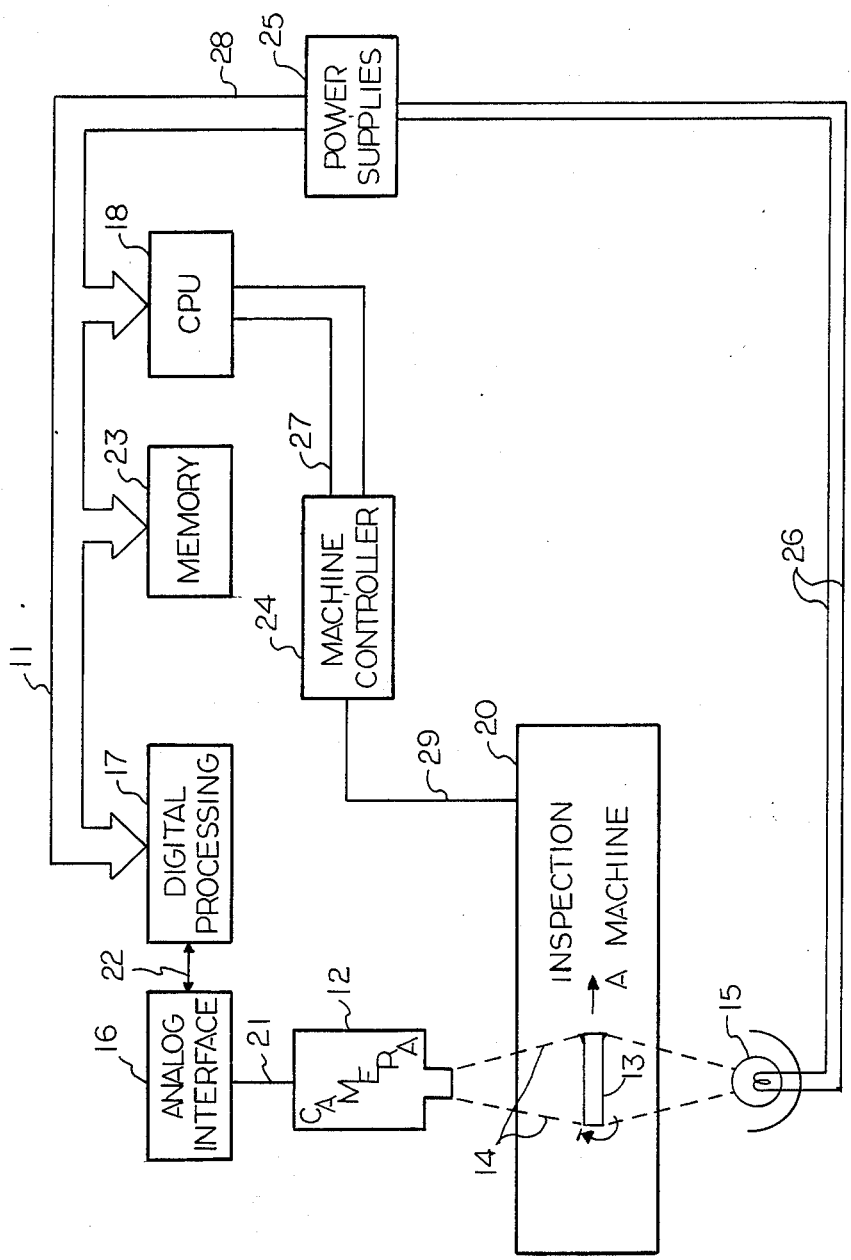
FIG. 1 is a system block diagram of the invention as applied to the inspection of tubular necks for cathode ray tubes by electro-optical image analysis according to this invention.

As shown in FIG. 1, the camera 12 has a field of view 14 encompassing object 13. Object 13 is back lit by a source of light 15 which, depending upon the optics employed, can provide bright field illumination of the object 13 in which the object appears bright and defects and inclusions in the object appear dark, or dark field illumination in which the object 13 appears dark and defects and inclusions in the object appear bright. In either arrangement, the camera is arranged to produce a video signal which is passed through an analog interface 16 to digital processing circuitry 17 which extracts information on distinctive parts of the scene viewed by the camera and makes it available to a central processing unit (CPU) 18 on the bus 11. The system is set up and controlled by the CPU 18 on the bus 11.

Distinctive parts of a scene, the defects and inclusions in object 13 are reported by the system to the CPU in data packets termed "events". Typically, there are so many fewer events than pixels, the row picture elements from the camera, that the events can be processed in software fast enough to keep up with a camera scanned at a four mega-pixel per second rate. The events are generated whenever the raw video signal or a filtered and/or log-amplified version of the raw video signal crosses operator-selected threshold values of signal magnitude representing deviations in light intensity emanating from discrete areas of the object from the background light intensity or gradients of light intensity as viewed by the camera.

The light intensity deviations result in signals identified by pixel source as a count of pixels along a scan sweep and by the sweep count. Signals derived from the pixel signals are identified by pixel number and sweep or row number. Like pixel members in different sweeps or rows are assigned to a column number and can be employed for two dimensional filtering. Thus in a camera having 2048 pixels in its linear array of detectors there can be 2048 columns of pixels.

According to one operating mode of the system, the values of signals applied to the thresholds are the combined outputs from high-pass filters that respond to brightness gradients in both the scan direction, i.e., from pixel-to-pixel, and in the scan-to-scan direction, i.e., along columns from a pixel in one scan to that pixel in another scan. The high-pass filter algorithm, operating on each pixel will subtract low-passed filtered version of each pixel's previous values in both row (scan) and column (scan-to-scan) directions from its current value. The resulting row and column high-pass filtered signals are then combined and applied to threshold patterns to generate events.

This two dimensional filtering of the video signals enables detection of light intensity gradients extending in any direction so as to expand image analysis capabilities and flexibility. As will be shown, filter time constants can be set to operator chosen values thereby enhancing the scope of applicability of video inspection systems. For example, an object 13 of circular cross section which is to be inspected for defects extending longitudinally as represented by light intensity gradients extending in the columnar direction as viewed by successive camera scans will cause events to be generated in the columnar direction and thus normal to the scan direction in the arrangement disclosed. Events from the row direction filter can be inhibited by operator chosen constants where it is desirable to ignore light intensity gradients in the row direction.

Pixel signals are processed in analog and digital form. Such signals are generated in analog form in the camera 12. Generally, an object having a circular cross section when scanned along an axis normal to the cross section will have a predetermined pattern of light intensity along the scan direction for all sweeps of the scan. Defects which alter the light by refraction, reflection, scattering and the like at discrete areas will cause deviations from the predetermined pattern. These deviations may be small relative to the total light intensity from the area in question and the general area proximate thereto.

When digitized, the deviations can be limited or lost due to the truncation of the digital signal by the limited number of bits available for its coding. Enhancement of the deviations can be achieved by subtraction of an image stored in a suppression RAM 43 ahead of the filters which ascertain events. The resulting difference image can be amplified to enhance the differences between the current image and the stored image on a pixel-by-pixel basis so that the digital encoding is applicable only to the difference signals rather than the full magnitude signals.

A general arrangement of one utilization of the digital filtering of video signals is disclosed in FIG. 1 wherein a line scan camera 12 is mounted to establish its field of vision 14 on an object 13 to be inspected. An inspection machine 20 manipulates object 13 and may include a conveyor (not shown) for moving object 13 incrementally in the direction of arrow A so that for an inspection interval it is maintained in the field of vision of the camera. Machine 20 rotates the object 13, illustrated as a cathode ray tube neck piece of transparent glass positioned so that its longitudinal axis is parallel to the field of vision 14, around its axis (by means not shown) to present the entire surface of the object to the camera. Object 13 is back lit by a lamp 15.

Camera 12 includes a linear array of photoelectric cells (not shown) each arranged to receive the light from a discrete area of the object to be inspected. The inspection areas extend along the object parallel to its axis. The camera array thus views a band extending the length of the object and when scanned repetitively while the object is rotated develops a signal for each scan representing the magnitude of light viewed by the camera for the areas scanned. The speed of rotation of the object, the camera scan rate, and the dwell time of the object in the inspection station can be correlated so that the camera views the entire outer surface of the object as a succession of scans made up of signals resulting from rows of pixel signals representing light from aligned areas extending along the length of the object and columns of pixel signals generated by successive scans from the signals from individual pixels during those successive scans representing light from aligned areas extending around the object, a circular band of such areas on a right circular cylindrical tube such as the major portion of the length of a cathode ray tube envelope neck.

Camera 12 when clocked to repetitively scan its linear array of light detectors issues a series of electrical signals on path 21 to analog interface circuits 16. These signals represent light viewed on the discrete areas of the object by the individual pixels and appears as a continuous signal issuing from a sample-and-hold circuit which when representing changes in light intensity from pixel to pixel will be stepped. Defects within or upon the object are sensed as abrupt changes in signal magnitude from the magnitude of a preceding signal. Changes in signal value are sensed as a function of the current signal magnitude and the preceding signal magnitudes. Past signal magnitudes are low-pass filtered and subtracted from the current signal to produce a high-pass filtered output signal. The low-pass filtered signal magnitude is the response of an infinite impulse response filter and approximates an exponentially weighted sum of the past signal values. Much of the filtering is accomplished in digital processing circuitry 17 coupled to the analog interface 16 by path 22.

A central processing unit 18 controls the camera 12, the digital and analog signal processing in 16 and 17, the inspection machine 20 and the inspection process over bus 11 which enables data and addresses to be passed between the CPU and the circuits. The CPU establishes filter standards for signal deviation enhancement, filter constants for the low and high-pass filters in both row and column dimensions for the inspection, threshold levels, vector forming operations, and inspection analysis at speeds compatible with the four mega-pixel per second scan rate of the exemplary system. Significant data are entered into the CPU memory 23 via bus 11 for processing. Power supplies 25 are coupled to object illuminating lamps 15 over leads 26, and the logic circuitry over bus branch 28. The CPU communicates over bus 27 to machine controller 24 which controls operation of the inspection machine 20 over cable 29.

Figure 2:
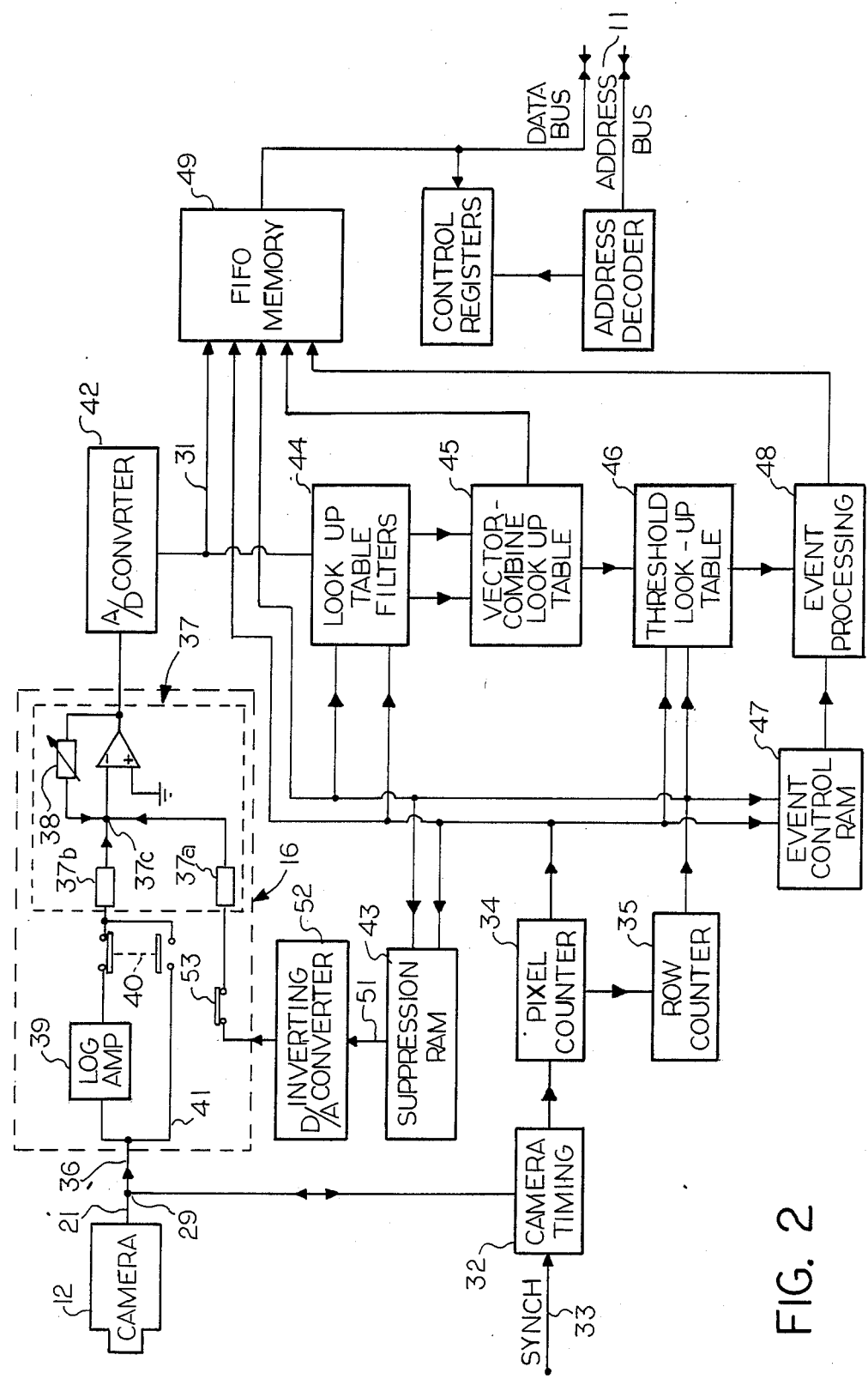
FIG. 2 is a system block diagram of the image analysis system of FIG. 1 showing the analog interface.

A more detailed disclosure of the analog interface system is shown in FIG. 2 wherein the camera 12 supplies signals and receives signals through junction 29 and signal path 21. Camera operation is controlled by a camera timing circuit 32 which generates the scan clocking for each sweep of the pixels in the camera linear array detector. Timing can be synchronized with the rotation of the object to be inspected through an external synchronizing signal source 33.

The data to be accumulated include the sweep or row count, the pixel count in the sweep, and the magnitude of the signal or the signal change. This information is translated to events if the change or absolute magnitude achieves the threshold value. The event identified by its magnitude, pixel number and row number location is passed to the CPU memory 23 for further processing in the CPU 18 as an evaluation of the object subject to inspection.

Pixel count is accumulated in pixel counter 34 which is reset at the end of each sweep of the linear array of pixels. Counter 34 counts the clocking pulses from camera timing circuit 32 which advance the scan from pixel-to-pixel. The number of the sweep or row count of pixels, is triggered at the end of a sweep to advance to the next row count as ascertained from the pixel counter 34 through the camera timing circuit 32 to the number of the current row in row counter 35.

Pixel counter 34 and row counter 35 are digital counters which issue digital signals indicative of the pixel and row from which the current video signal value is generated.

Raw video signals in analog form pass on path 21 are passed through junction 29 and path 36 to the analog video processing section 16. The signal is a pixel-by-pixel sampling of pixel signals in a series, each pixel signal being identified by its pixel source in the count of counter 34. The system is arranged to pass pixel signals directly through to the summing operational amplifier 37 which has a programmable gain feature. Alternatively, the signals can be routed through a logarithmic amplifier 39. Commands from the CPU determine this signal routing. A standard group of pixel signals introduced by the CPU through a suppression RAM 43 can be subtracted from the incoming camera signal to the operational amplifier 37.

Video signals of a scan are passed to an analog to digital converter 42 and the digitized signals are passed to the filters 44. The filters 44 pass the filtered signals to a vector-combine look-up table 45, resulting in a signal which is operated upon to evaluate if it is to be classified an event in threshold look-up table 46, event control RAM 47 and event processing section 48. Event signals are passed to a first-in-first-out stacked memory, FIFO, 49 which can pass the signal to the CPU 18 on bus 11 for use in the inspection.

A threshold pixel signal value can be set as the effective signal level so that the initial portion of the camera scan or pixel signal series is disregarded to mask out spurious signals at the beginning of the scan or optical irregularities to the edge of the scene. This threshold value and its implementing circuitry is not shown.

While the pixel signal series can be routed through path 41, effectively applying raw pixel signals to the analog-to-digital converter 42, in the CPU dictated state illustrated by switch 40, the signals are passed through a logarithmic amplifier 39 to produce illumination invariant signals. Thus, pixel signals for discrete areas of the image with like contrast ratios to adjacent discrete areas will have like output signal level differences from amplifier 39 for all background light intensities.

Another option for suppressing standard image pixel signal values and detecting only anomalies in the image of an object being inspected is to subtract the standard image pixel signals corresponding to the incoming pixel signals so that only the difference signals are applied to A/D converter 42.

In setting up the system for inspection of a multiplicity of similar objects, a standard object signal pattern is established comprising a signal magnitude for each pixel of a scan of a standard object free of defects. This signal pattern is stored in a reference signal memory 43, designated suppression RAM, as a digital magnitude for each pixel of a standard object sweep. This digital magnitude may be defined by eight bits and stored at respective pixel addresses in the memory 43.

As the scan progresses from pixel-to-pixel with switch 53 closed to utilize the suppression process, reference signal memory 43 is addressed by pixel counter 34 to issue a digital reference signal intensity value for that pixel over path 51 to inverting digital to analog converter 52. The resultant inverted analog signal from converter 52 is passed to the analog video processing circuit 16. The standard signal intensity value in analog form and inverted is applied via switch 53 to scaling resistor 37a of operational amplifier circuit 37. The raw video signal from camera 12 or its logarithmic amplified value is applied through scaling resistor 37b to summing mode 37c at the input of operational amplifier 37 causing the amplifier to issue a signal which is the difference between the scan reference signal intensity for that pixel and the actual sensed pixel signal intensity. That difference signal is applied to the analog-to-digital converter 42. The resulting digitized difference signal is operated upon by the filters 44 to identify events. Operational amplifier gain can be adjusted at resistor 38 to enhance the difference signals.

The suppression RAM 43 is loaded through the CPU 18 and bus 11 by running a scan of a defect free object through the camera 12, the analog video processing circuitry 16, the A/D converter 42, path 31, the FIFO 49, the CPU 18 and into the suppression RAM 43. The resultant magnitude data are placed at the appropriate addresses throughout this manipulation by the address afforded by the pixel counter 34 operating in synchronism with the pixel signal generation. Where two dimensional referencing of the reference video signal is to be provided, a multiple scan sequence of a moving object, for example by rotating the neck 13, can be undertaken in conjunction with addressing of the suppression RAM 43 by both the pixel counter 34 and row counter 35. The suppression RAM 43 and the operational amplifier 37 can be employed as the source of video data supplied directly to the CPU for image analysis on path 31 or it can be combined with the high-pass filtering as accomplished by look-up tables as selected through the CPU.

Figure 3:
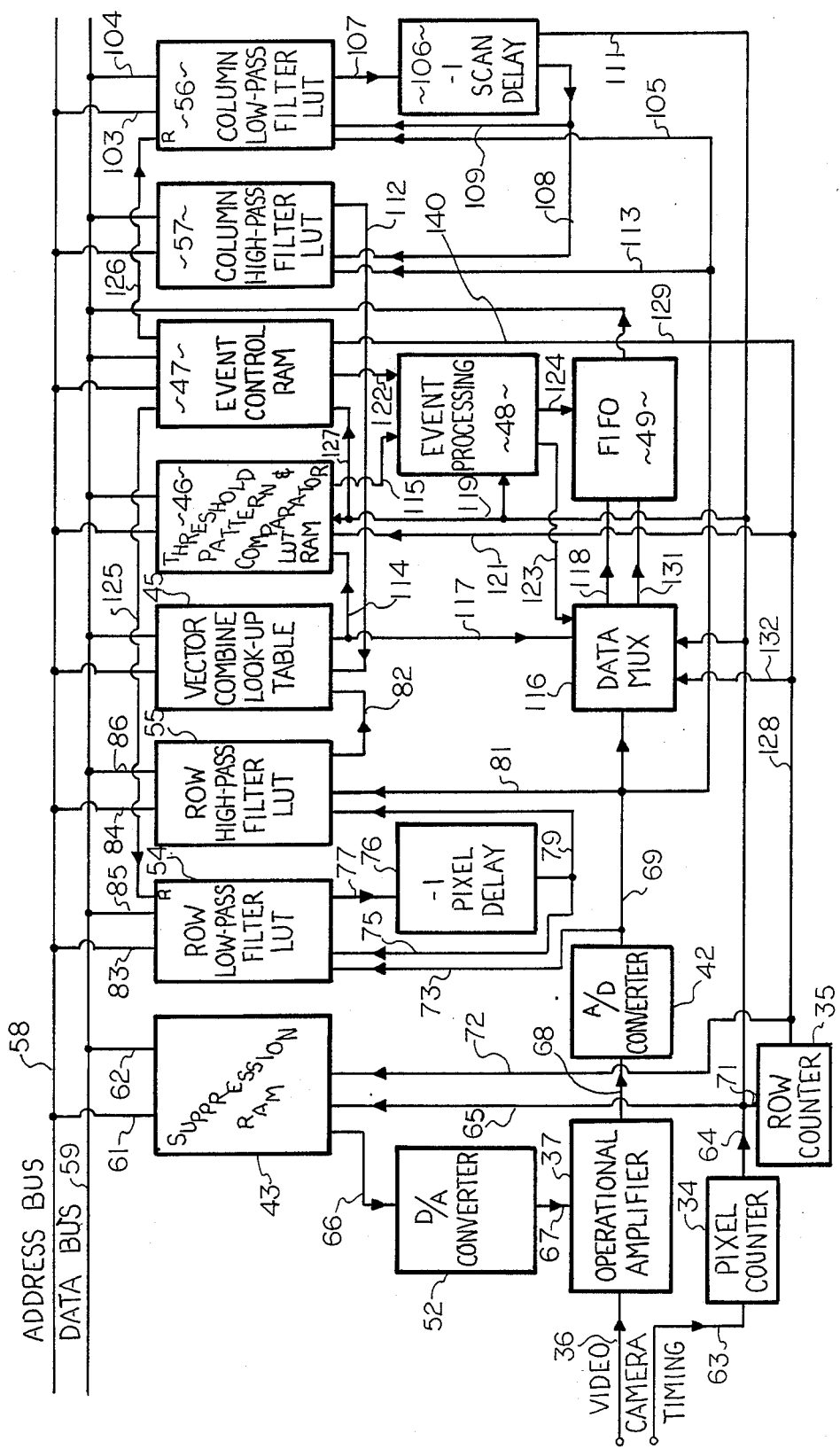
FIG. 3 is a block diagram of the digital processing system of FIG. 1 in greater detail.
Figure 4:
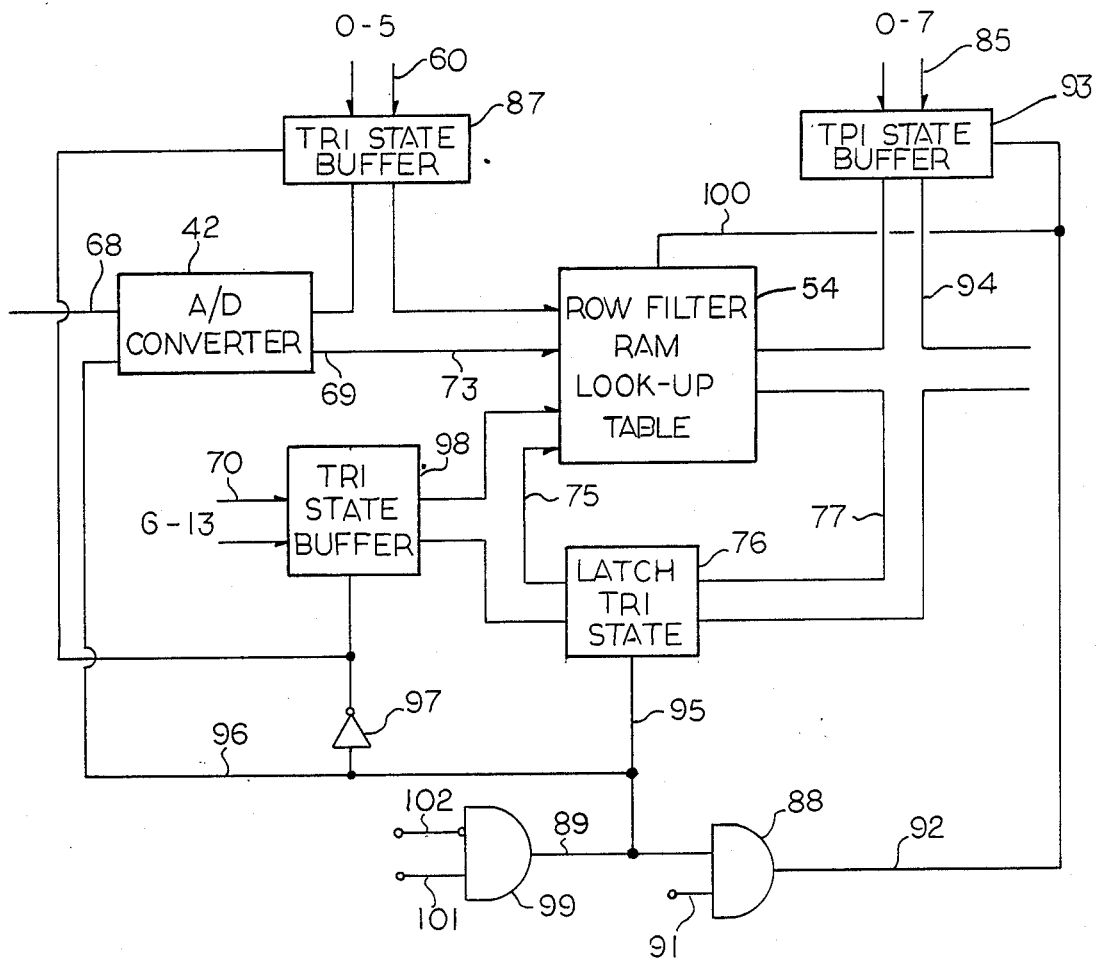
FIG. 4 is a diagram of a typical system for loading computer generated values for all possible input values to a look-up table in a RAM, the row low-pass filters in one form of this invention.

Digital filtering is accomplished by means of look up tables which afford an infinite impulse response filter and thus can have any corner frequency. Generally the time constants chosen are long relative to the scanning rate so that the filter's response to a step change in the sensed light intensity decays over an interval exceeding the scan of the maximum anticipated pixel count in a sensed defect in the object. The filters 44, as shown in greater detail in FIGS. 3 and 4, comprise a row low-pass filter 54, a row high-pass filter 55, a column low-pass filter 56, a column high-pass filter 57, a vector-combine memory 45, and a threshold memory 46, all of which utilize look-up tables set by the CPU 18 according to operator selected constants and functions. FIG. 3 shows the general organization of the digital processing section of FIG. 1 and the combination in FIG. 2 of filter 44, threshold look-up table memory 46, an event control RAM 47, event processing circuit 48 and the FIFO 49 from which the digital processed events are advanced to the bus 11 and the CPU 18 and its memory 23.

In FIG. 3 camera video signals, the series of individual pixel signals are fed to operational amplifier circuit 37. Optionally standard signal magnitudes for the respective pixels are subtracted from these incoming signals. These standard signal magnitude are set in suppression RAM 43 from bus 11, more particularly the pixel identification is fed on address bus 58 and the signal magnitude for that address is fed on data bus 59 from CPU 18 through paths 61 and 62 to the suppression RAM. As the camera array is scanned, camera timing signals on lead 63 advance pixel counter 34 in synchronism with the applied raw video signals for the pixels on path 36. Pixel counter 34 issues a digital count to suppression RAM 43 on paths 64 and 65 causing RAM 43 to issue on path 66 the preset standard intensity values for the raw pixel signal then imposed. The digital signal on path 66 is converted in D/A converter 52 to an analog signal compatible with the raw video signal and passed on lead 67 to operational amplifier 37 which issues a signal representing the difference between the raw video of the pixel and the standard signal intensity for the pixel on lead 68 to A/D converter 42. Path 68 to A/D converter 42 may have its signals amplified as explained with respect to FIG. 2. Signals from the A/D converter are then advanced in digitized form on path 69 either directly to the system's stacked storage 49 for analysis by a CPU or to the high-pass filters for processing as the extracted information concerning the image anomalies.

In the preceding description, a cylindrical object having a similar standard pixel signal pattern for all rows has been assumed. If successive standard scans have varying standard pixel signal patterns, they can be taken into account by providing those patterns, addressed by row count, in the suppression RAM. Row count can be derived from the pixel counter 34 and the count issued on path 64 by means of row counter 35 which advances in response to one of the terminal pixel counts in a row of pixels applied from path 64 to path 71. The row count is issued digitally on path 72 from row counter 35 to suppression RAM 43 and is utilized in selecting the standard pixel pattern for the row subject to current scanning. In such an arrangement, the object camera and the row count should be initialized so that the pixel signals of the camera for the row being scanned correspond to the selected standard pixel signal intensities for the row as set up in the suppression RAM by the CPU. Further, the rows counted are to be kept in synchronization to the scanned row on the object as the image analysis proceeds.

Images represented by camera video signals are high-pass filtered in both the row and column directions and are combined into a single value termed a "vector". Incoming video signals are low-pass filtered by means of RAM look-up tables and the output of the low-pass filter is subtracted from the current pixel intensity to provide high-pass filtering by means of RAM look-up tables.

Low-pass filtering of the row, scan direction, signals is by adding a fraction of the preceding low-pass filter output to a fraction of the current pixel signal magnitude subject to constants which are operator selectable. Video signal magnitudes are applied on path 73 as six bits addressed to the row low-pass filter 54 containing a RAM loaded as a look-up table which also receives eight bits of address on path 75 from the one pixel delay latch 76 connected to the low-pass filter by path 77. The output of the row low-pass filter at path 77 can be expressed as:

$$G(r,c) = J*F(r,c) + (1-J)*G(r,c-1)$$

where

F(r,c) is the current filter input, the pixel signal intensity, at path 73 from A/D converter 42, G(r,c−1) is the filter output at the previous pixel in the current scan, from latch 76 (on path 75), G(r,c) is the current filter output 77, and J is a number between zero and one.

The filter output at the previous pixel signal out of latch 76 is applied to address inputs of both the row low-pass filter 54 containing a RAM loaded as a look-up table and row high-pass filter 55 containing a RAM loaded as a look-up table at paths 75 and 79 respectively. The current pixel signal intensity is applied to row high-pass filter 55 at path 81. To complete the row high-pass or gradient filter 55, the row low-pass filter output is subtracted from the current pixel intensity according to the equation:

$$F(R) = L*F(r,c) - M*G(r,c-1),$$

where

F(R) is the row high-pass filter output at path 82, and

L and M are operator selected numbers.

It will be noted that the pixel signals are applied as addresses to 16K by 8 RAMs which will accommodate look-up tables for all possible combinations of F(r,c) and G(r,c-1) for operator selected values of J, L and M. These tables are obtained by a software routine from the CPU 18 loaded from the bus 11 on paths 83 and 85 for 54 and 84 and 86 for 55. The look-up tables in each filter provide preset outputs appropriate for the fourteen bit address provided by the combination of the six bit input address obtained from the current pixel signal magnitude and the eight bit input address obtained from the low-pass filtered prior pixel signal. The resultant filters are infinite impulse response filter which can have any corner frequency.

The set up of the look-up table in row low-pass filter RAM is controlled from the CPU. As shown in greater detail in FIG. 4, the RAM look-up table feed on path 73 can be loaded from a local counter for row filter RAM Look-up table 54 controlled by signals from the CPU. The address bits 0–5 are passed from the local counter and bus 60 through a tri-state buffer 87. The address bits 6–13 are similarly loaded from a local counter through bus 70. A CPU write condition is developed in AND 88 by a combination of a tri-state control signal on lead 89 and a CPU write signal on lead 91. AND 88 issues the write signal on lead 92 to a tri-state buffer 93. Data issued during the computer routine for loading values of G(r,c) in the look-up table 54 is passed from bus 11 to branch 85 as bits 0–7 generated by the software calculation in CPU 18. These calculated values are passed through tri-state buffer 93 to branch 94 of path 77 while the write signal on lead 92, branch 100 enables RAM 54 to receive the CPU generated data.

Latch 76 and A/D converter 42 are inhibited during this loading of the look-up table by being tri-stated by tri-state control on lead 89 through branches 95 and 96 while inverter 97 enables the buffers 87 and 98. The tri-state control is afforded by AND 99 when a true signal is imposed on its input 101 and a false signal is present on its inverting input 102.

When J is set to one the equation for the low pass filter output G(r,c)=J*F(r,c) and the output of the row low-pass filter is simply the input.

Column or scan-to-scan filtering deals with the relationship of pixel signal magnitudes for the same pixel in scans of proximate rows. As with the row low-pass filtering, column low-pass filter 56 involves a dual ported memory look-up table. Filter 56, as shown in FIG. 3, has address and data ports 103 and 104 from the bus 11 for filter logic control and loading the table. Signals are passed from the video signal source lead 36 and/or suppression RAM 43, via the A/D converter 42 on paths 69 and 105. The one row scan delay 106 receives output signals from low-pass filter look-up table 56 on path 107 and applies its output, the low-pass filter for the currently scanned pixel when it was scanned in the preceding row on path 108 and branch 109. The low-pass filter look-up table 56 is set to issue a signal for the sum of a fraction of the current pixel signal magnitude on 105 and the fraction of the output for the current low-pass filtered output for the current pixel signal for the preceding scan on path 109. The current pixel signal count is identified for the one scan delay 106 by pixel counter count from path 64 to path 111. Video signal pixel magnitudes are applied to column low-pass filter 56 on path 105 as six bit codes for the pixel currently scanned and the low-pass filtered signal for the corresponding pixel in the prior scan is applied by the one scan delay RAM 106 to address port 109 as eight bit codes and returned to RAM 106 from filter 56 as an eight bit code on path 107.

The column low-pass filter corresponds generally in form and function to the row low-pass filter with the substitution of the stacked memory for each low-pass filtered pixel signal of the preceding scan provided by −1 scan delay 106, including a dual 16K×8 RAM, which is substituted for the latch 76. A software routine calculates and down-loads values of the current filter output for all possible combinations of the current pixel signal magnitude inputs to the low-pass column filter look-up table with all possible filter outputs for the current pixel position in the previous scan. Thus, the look-up table in the RAM 56 provides the column low-pass filter signals in response to address combinations at path 105 for the current pixel signal and path 109 for the filter output for the current pixel position in the previous scan according to the equation:

$$H(r,c) = K^*F(r,c) + (1-K)^*H(r-1,c)$$

where

F(r,c) is the current filter input, the pixel signal magnitude at path 105,

H(r−1,c) is the filter output for the current pixel position (column) in the previous scan, the filtered signal at path 109, H(r,c) is the current column low-pass filter output, the filtered signal at data path 107, and K is the column low-pass filter constant, a number between zero and one.

The value of K is operator selected. When K is 1, the output of the column low-pass filter is simply the pixel-to-pixel intensity difference or gradient in the column direction.

The column high-pass filter 57 subtracts the output of the −1 scan delay 106 from the current pixel signal intensity to produce a high-pass filtered output for the current pixel signal on path 112. Current pixel signal intensity is applied to filter 57 on path 113 as a branch from path 69 from A/D converter 42. The low-pass filtered output for the pixel signal delayed one scan is applied to filter 57 on path 108. The filtered value as stored in a look-up table in the column high-pass filter is pre-calculated by the CPU and loaded in a RAM in the filter in the same manner as described for the row low-pass filter 54 with respect to FIG. 4 to provide all solution values for all possible inputs of the current pixel signal intensity and the low-pass filter output for the current pixel for the preceding scan of that pixel according to the equation:

$$F(C) = P^*F(r,c) - Q^*H(r-1,c),$$

where

F(r,c) is the current filter input,

H (r−1,c) is the filter output for the current pixel position (column) in the preceding scan, and P and Q are operator selected numbers.

In this equation, when P and Q are 1, the filter 57 is a straight high-pass filter. Where P is 1 and Q is zero, the filter 57 passes the row or log-amplified image unchanged. Where P is zero and Q is 1, the filter 57 has an output the same as the column low-pass filter output.

A single magnitude value of six bits is derived from the row high-pass filter output on path 82 and the column high-pass filter output on path 112 in a vector-combine section 45 utilizing a look-up table computed by the CPU and down-loaded into a RAM in the vector-combine section according to the equation:

$$V(r,c) = \text{a function of } R^*F(R) \text{ and } S^*F(C)$$

where

R and S are operator-selected constants, and the function is software-determined, e.g., the square root of the sum of the squares or the sum of absolute values.

R and S are gains applied to the row and column high-pass outputs. One direction can be emphasized over the other. If one is zero, the vector combination, V(r,c) will only contain information about the direction corresponding to the other, e.g. with R zero only intensity gradients or changes in the column direction will be reflected in V(r,c).

The threshold pattern and comparator 46 includes a look-up table which contains 64 one-bit entries for each of 4,096 "super cells". The 64 bit per super cell are pre-calculated outputs for each of the magnitudes possible in the six-bit input on path 114 from the vector-combine section 45 to threshold section 46. The output is a single bit, an event, issued on path 115 to the event processing section 48. Super cells can be defined as either one-dimensional or two-dimensional. One-dimensional super cells cover 4 successive pixels within each scan to provide 4,096 super cells covering scans up to 16,384 pixels long. Two-dimensional super cells each subsume a rectangular array of pixels defined by 4 pixel groups by 4 scan groups. The number of pixels in a two-dimensional super cell will depend on the number of pixels per pixel group and scans per scan group. A scan group counter (not shown) can be set with 1, 2, 4, 8, 16, 32, 64 or 128 scans in each group and a pixel group counter (not shown) can be set to have similar numbers of pixels. As in the one-dimensional case, there are 4,096 two-dimensional super cells. Two-dimensional super cells are arrayed 64×64.

The 64 bits pre-loaded in threshold and pattern comparator 46 by the CPU for each super cell can mimic a comparator with a threshold set. For example, at a threshold of 32, the bits for levels 0 through 31 could be set at zero and the bits for levels 32 through 63 could be set at 1. If bits for all 64 levels in a super cell are zeroed, all pixels within the super cell would be masked out. Another setting could place intermediate levels, e.g., 20 through 40, set to zero. In that setting, bits for levels above 40 and below 20 would be set to 1. This arrangement could be used to detect extreme positive and negative excursions of a bi-polar signal translated to be all positive before analog-to-digital conversion.

Events are generated based on the state of the 1-bit output of the threshold pattern and comparator section 46 look-up table. A software routine computes and down-loads a 1-bit value for each possible value of the vector combine 45 output V(r,c), in groups of a predetermined number of pixels in the image of up to 4,096 groups. This predetermined number of pixels is chosen to spread 4,096 intervals uniformly over all pixels of a scan. A 128K×1RAM permits a variety of threshold configurations. One such configuration involves one positive and one negative threshold pattern for each pixel so that the output is one above an upper value of V(r,c), zero between it and a lower value and one again below the lower value. This arrangement can be applied to the signal output of one of the high-pass filters passed straight through.

The threshold pattern and comparator look-up table receives a vector combine value for each pixel signal which has been high pass filtered by row and/or column high pass filters 55 and 57. Each of the pixel signals is designed to a super cell. Each super cell sets thresholds for its pixels. Hence, the super cell settings, which are software determined by the CPU 18 and operator selected parameters, establish a go-no-go standard for the vector-combine values for each pixel it contains.

Vector magnitude signals are also passed to data multiplexer 16 in 6-bit form on path 117 from the vector combine section 45 as one source of magnitude signals to be supplied to FIFO 49 over path 118. The video signal magnitude on path 69 is another source of such data for the FIFO.

Threshold pattern and comparator 46 passes event signals defined by the CPU set values in the look-up table to event processing sector 48 on path 115. The pixel identification in 46 is established by pixel count path 119 from counter 34 and row count path 121 from row counter 35.

Event control RAM 47 controls events passed to event processing section 48 by output path 122. Section 48 in turn issues control signals to the data multiplexer 116 on path 123 and to FIFO 49 on path 124 to determine when events are to cause data entries into the FIFO memory stack.

Event control RAM 47 is set up by the computer with one or two-dimensional spatial pattern by which event generation is modified and controlled. For each region of the image, the event control RAM determines if the row filter should be initialized. In the regions of the image where this is done, the row low-pass filter 54 is set to the current input pixel value on path 125 so that the output of the row high-pass filter is zero. This initialization is appropriate at the beginning of a row or the beginning of a region of interest to prevent spurious signals which might be read as events from these discontinuous filter inputs. In all regions where the row filter is initialized, there will be no row high-pass filter contributions to events. Similarly, the column low-pass filter 56 can be initialized over path 126.

Event control RAM 47 comprises two 16K×8 byte arrays. The fourteen address bits to each array comprise seven bits of the pixel group count derived from pixel count path 127 and seven bits of the scan group derived from row counter 35 over path 128 and 129. The event control RAM 47 is filled by the CPU 18 which places data on the bus data lines 59 while pulsing auxiliary pixel or row counters (not shown) that supply the address inputs to the control ram.

RAM 47 contains storage for 64K nibbles (4 bits each) of event control data. One bit initializes the row low-pass filter, a second bit initializes the column low-pass filter, a third inhibits events, and the fourth invokes run-length encoding. As the system sequentially processes pixels and scans applied on paths 127 and 129, the RAM is addressed by the current pixel group count and scan group count. Thus, each nibble in the RAM corresponds to a uniquely paired pixel group and scan group. Since there are 256 each of pixel groups and scan groups, the RAM can be considered to store a two-dimensional pattern having 256×256 or 64K cells. As noted above, each of the pixel and scan groups may be independently selected to be 1, 2, 4, 8, 16, 32, 64 or 128. For examples with 8 pixels per pixel group and 16 scans per scan group, the event control RAM will handle 4,096 scans (256×8).

In addition to low-pass initialization for the row and column filters (pixel scan direction and successive scans direction), the event control RAM 47 enables storage of events in the FIFO memory 49 while processing pixel signals for pixels in the current cell. RAM 47 can be set to disable a cell, thereby masking those image anomalies which might have been read as events for pixels assigned to that cell. It also selects run length encoding within the current cell so that when there are three or more events in a sequence of a row only the first and last of the string is placed in the FIFO memory 49, thereby reducing the amount of data placed in the FIFO for the CPU to process. Alternatively, without run length encoding effective every event in a sequence of pixels having signals at event levels is stored in the FIFO.

Event data is utilized in the event processing section 48 to control the flow of appropriate data to the FIFO memory 49. The nature of the data stacked in the FIFO is determined in the event processing station 48 and its source is determined over path 123 by control of the data multiplexer 116. Multiplexers 116 responds to event processing control 48 enabling the multiplexer to pass data over paths 118 and/or 131 to the FIFO.

Data multiplexer controls the passing of video magnitude data from A/D converter 42 on path 69 and filtered vector-combine magnitude data from look-up table 45 on path 117 to FIFO 49. It also controls the application of the pixel count and the row count to the FIFO.

The FIFO memory receives and stores event data and delimiter data. Delimiter data can be identification of the initiation of analysis of a scene when a new object is to be inspected, or the number of the row or scan in which an event was detected and stored. Such information triggered by logic (not shown) in part employs row count information from row counter 35 passed from path 128 to data multiplexer 116 over path 132 and into the FIFO 49 on path 131.

When events are detected, assuming no masking of the area, the following data are entered in the FIFO.

1. a bit identifying the entry as event data on path 124 from the event processing station 48 and thus distinguishing the data from delimiter data;

2. the pixel number in the image, the pixel or column count; and 3. the intensity of the unfiltered image, F(r,c), on path 69 as raw video or the vector combination signal on path 117 (r,c), as selected by software and thence through multiplexer 116 on path 118.

Event control RAM 47 is pre-loaded with the desired cell structure and the desired control bits or each cell from the CPU 11. Thus, the CPU offers a wide range of variations in the control of the processing of video signals including direct reading of pixel signals into the FIFO, reading of the signal from which a standard signal has been subtracted, a reading of a row high-pass filtered signal, and a reading, a vector combined row and column signal each of which has been filtered. In addition, the video signals can be logarithmically amplified to provide illumination invarient video signals. Constants can be set through the CPU to emphasize one direction of filtering over the other even to the extent of restricting the filtering to but one direction. Different "event" thresholds can be established for the various areas of the scene subject to analysis. These areas, the super cells of the threshold pattern and comparator 46, can be set up in a RAM or look-up tables with individual threshold levels for the magnitude in the super cells which will be processed as an event. Further flexibility of analysis is afforded through CPU control in the event control RAM 47 and the event processing section 48 whereby cell areas are defined and those cells can be masked selectively, can be read on a run length encoding basis selectively, and can be arranged for filter initialization.

The data stacked in the FIFO memory 49 is read out to the bus 59 and to the CPU 18 and/or its memory 23 for processing into useful inspection information with respect to objects 13 in the inspection machine 20. Such inspection information can be employed to classify the inspected objects 13 and control the machine 20 through machine controller 24 so that unacceptable objects are rejected by the machine.

The FIFO 49 functions as a defect accumulator that makes defect data available to the CPU 18 which in turn makes and reports appropriate process decisions with respect to the object 13 being inspected. After the high-pass filter is checked against a pattern of thresholds in threshold pattern and comparator look-up table 46, "events" are generated for those pixels with filtered intensities above the thresholds. The event control RAM 46 provides selectability of pixel cells which mask the "events" for pixels which they contain. "Events" which are not masked are loaded into the FIFO buffer memory for access by the CPU and its associated software.

The CPU software analyzes this data for size, location, connectivity and other attributes. On the basis of this analysis, an "accept" or "reject" decision is reached and communicated to the inspection machine 20 via its machine controller 24.

The software can retain statistical information or rejects. The CPU can be arranged with diagnostic modes to allow for computer graphics presentation of relevant vision and image processing data. Scope display of data is employed to evaluate the settings of filter constants, the settings for masking areas such as those in which optical changes are either insignificant to the quality of the object or are spurious in the inspection process, and the settings for thresholds. Such evaluations may indicate the need for certain parameters of the system or look-up tables be reset to appropriate values.

In one mode of inspection operation the image analysis system is operated in a data compression mode in which only significant deviations from background or "events" are recorded. The CPU 18 then transfers this information from the FIFO to computer memory 23 for further analysis. Once the data are stored the image analysis system is ready to acquire new data for the next inspection cycle.

The information stored in computer memory 23 consists of an array of data points which contains the pixel or camera diode number, the sweep or row count number, and magnitude of deviation from background for each event. Computer processing is performed so that data points which are close together, as a function of pixel and row number, become members of a single "blob". This is accomplished in a two-step process. First, "events" on the same row are analyzed to determine if they are close enough to be linked into a "string". This process continues until all "events" have been assigned to "strings". Then, "strings" are processed to form "blobs". A "string" is assigned to a "blob" by checking its distance to "strings" that have already been assigned to that "blob". This process continues until all "strings" have been assigned to "blobs".

Various string attributes are employed in "string" generation, including first "event", last "event", "blob" assignment number, "string" weight (the sum of the event magnitudes) and a pointer to the next "string" in the "blob". When a string is formed, first "event" is equal to the number of the first "event" in the "string", the "string" weight is set equal to the magnitude of the first "event", and the "blob" number is unassigned. When an "event" is added to the "string", the "string" weight is increased by the magnitude of the "event". This continues until an "event" is found that does not belong to the "string". At this time, the previous "event" number is assigned to the last "event" attribute and a new "string" is created.

"Blob" attributes are used in conjunction with the "string" attributes for "blob" generation. "Blob" attributes include the first "string" of the "blob", the number of "strings" in the "blob", the "blob" weight (the sum of the "string" weights for that blob), and the number of "events" in the "blob", "blob events". "Blob" generation begins by assigning the first "string" to the first "blob". The remaining "strings" are checked to see if they can be assigned to this "blob". If a s"string" is assignable, the next "string" attribute of the first "string" is set to the new string and the new string is assigned to "blob 1". The number of "events" attribute for this "blob" is incremented by the number of "events" in the "string" and the "blob" weight attribute is increased by the "string" and the "blob" weight. When no more "strings" can be assigned to the first "blob", a new blob is created using the first unassigned "string" and processing continues until all "strings" have been assigned to "blobs". Checking is then done to determine if two "blobs" should be joined since defect shapes can be quite arbitrary.

With the completion of "blob" generation, a determination of whether or not to accept the object 11 being inspected is made. "Blobs" below a certain size may be ignored. "Blobs" with fewer "events" than a minimum "event" inspection parameter may be ignored. The size and spacing of "blobs" is considered in the evaluation.

Several different tests are performed to determine whether or not the attributes of a given "blob" was a rejection of the object being inspected. The number of "events" in the "blob" is tested to ascertain if it exceeds a limit. The location of the "blob" on the object may enter into the number of "events" which are acceptable. The density of "blobs" is measured and if excessive is grounds for rejection. The dimensions of the "blobs" are measured e.g. in the x and y dimensions. "Blob" size and spacing can be measured as in the scan direction and perpendicular to it so that small "blobs" too close together become the basis for rejection. Various combinations of the criteria can be considered in the rejection or acceptance decision.

The image analysis system of this invention lends itself to many variations in view of the flexibility of its architecture. As set forth above, sections of the system are available at the operator's option. Some of these sections are selectively switched into the image processing path while others are rendered effective on the basis of operator selected constants. Operator control is afforded through the CPU. One optionally utilized section is the suppression RAM 43 which is CPU loaded as from a standard object employed as a camera image source to produce standard image pixel signal values on a pixel-by-pixel basis. The suppression RAM cooperates with means to count pixel signals from an inspection image, pixel counter 34, and means to compare pixel signals, operational amplifier circuit 37 for given counts defined by the counting means and issued by the means to sample the camera 12, with standard image pixel signal values from the suppression RAM for the given pixel count to form a comparison signal. The output of circuit 37 can be passed directly through A/D converter 42 to the FIFO 49 for outputting to the CPU or can be further processed in the filters, vector-combine, and event processing sections prior to inputting to the FIFO.

Pixel signals are digitized at a finite number of intensity levels in A/D converter 42 with variable gain amplifier adjustment of the A/D converter input to achieve full range operation, as the six bit output of converter 42. Such a finite number of signal levels enables filtering of the video signal results by means of look-up tables down loaded into RAMs for all values of the digitized pixel signals. Such filters include row low-pass filter look-up table 54, row high-pass filter look-up table 55, column low-pass filter look-up table 56 and column high-pass filter look-up table 57.

Vector-combine results from the combination of the row and column filter outputs also are implemented by precalculated values for all possible input values in a look-up table in a RAM loaded under control of the CPU. This approach includes means to identify each pixel by row and column for which a vector-combine output is produced. It can be weighted by choice of constants applied to the row and column input values.

Further use of look-up tables is taught in the threshold pattern and comparator section 46 wherein a first set of groupings of proximate pixels by row or by row and column is employed to define cells, termed "super cells" above, for the setting of threshold values employed in designating vector-combine signal levels as characteristic event signals for the detection of anomalies in the inspected object image. Thus different threshold values can be set for individual cells to accommodate variations in the image areas. Again, a grouping of pixel rows and columns is provided for cell designation in the event control RAM 47. As in section 46 the grouping is operator selected through the CPU. CPU control of thresholds in section 46 is provided. In event control ram 47 the setting of cell functions of pixels assigned the cells can include masking, run-length encoding of strings of event signals, and filter initialization for the pixel signals.

It is evident from the preceding discussion of options available in the image analysis system that the specific examples set forth above are merely illustrative of the invention and are not to be read in a restrictive sense.

What is claimed is:

1. In an image analysis system comprising a camera having a linear array of pixels each providing a signal representing the magnitude of light received from a corresponding discrete area along a band of discrete areas on an object producing said image; means to sample said pixel signals serially; means to extract a signal information on distinctive parts of the image; and means to process said extracted signal information for utilization by a computer, the improvement comprising: means to digitize pixel signals at a finite number of intensity levels; and means to filter the digitized pixel signals according to a look up table defined by an algorithm for all values of intensity of said digitized pixel signals stored in a memory; wherein the filter comprises a low pass filter having a signal intensity which is a function of the currently scanned pixel signal as a first input and a second input which is a function of a preceding scanned pixel signal, and a high pass filter having an output which is a function of the signal intensity of the currently scanned pixel signal less a quantity which is a function of the low pass filter output for a preceding scanned pixel signal.

2. In an image analysis system comprising a camera having a linear array of pixels each providing a signal representing the magnitude of light received from a corresponding discrete area along a band of discrete areas on an object producing said image; means to sample said pixel signals serially; means to extract signal information on distinctive parts of the image; and means to process said extracted signal information for utilization by a computer, the improvement comprising: means to digitize pixel signals at a finite number of intensity levels; means to repetitively operate said means to sample said pixel signals serially to provide a plurality of signal series representing the magnitude of light received from respective corresponding discrete areas along a plurality of adjacent bands of discrete areas on an object producing said image; means to identify each pixel signal in a series; means to filter signals arranged to filter signals made up of the digitized pixel signals of like identity, as defined by said means to identify, in successive series of pixel signals according to a look-up table stored in a memory and defined by an algorithm for all values of intensity of said digitized pixel signals defined according to the equation:

$$K(r,c) = K*F(r,c) + (1-k)*H(r-1,c),$$

where

F(r,c) is the current filter input signal,
H(r−1,c) is the filter output for the current pixel identity in a preceding series of pixel signals,
H(r,c) is the current filter output, and
K is a number between zero and one determining the time constant of the filter.

3. In an image analysis system comprising a camera having a linear array of pixels each providing a signal representing the magnitude of light received from a corresponding discrete area along a band of discrete areas on an object producing said image; means to sample said pixel signals serially; means to extract signal information on distinctive parts of the image; and means to process said extracted signal information for utilization by a computer, the improvement comprising: means to digitize pixel signals at a finite number of intensity levels; means to repetitively operate said means to sample said pixel signals serially to provide a plurality of signal series representing the magnitude of light received from respective corresponding discrete areas along a plurality of adjacent bands of discrete areas on an object producing said image; means to identify each pixel signal in a series; means to filter signals arranged to filter signals made up of the digitized pixel signals of like identity, as defined by said means to identify, in successive series of pixel signals according to a look up table stored in memory and defined by an algorithm for all values of intensity of said digitized pixel signals which produces low-pass filtered signals for said pixel signals and including a second memory having a second look-up table defining high-pass filtered signals as the difference between a function of said currently sampled pixel signal intensity and a function of said low-pass filtered signal for said current pixel identity in the preceding series of pixel signals.

4. An image analysis system according to claim 3 including a computer for loading said second memory with said second look-up table.

5. An image analysis system according to claim 3 second look-up table defines signal values according to the equation:

$$F(C) = P*F(r,c) - Q*H(r-1,c),$$

where

F(r,c) is the current filter input,

H(r−1,c) is the filter output for the current pixel identity in the preceding series of pixel signals, F(C) is the current filter output, and P and Q are numbers between zero and one.

6. In an image analysis system comprising a camera having a linear array of pixels each providing a signal representing the magnitude of light received from a corresponding discrete area along a band of discrete areas on an object producing said image; means to sample said pixel signals serially; means to extract signal information on distinctive parts of the image; and means to process said extracted signal information for utilization by a computer, the improvement comprising: means to digitize pixel signals at a finite number of intensity levels; means to filter the digitized pixel signals according to a look up table defined by an algorithm for all values of intensity of said digitized pixel signals stored in a memory; wherein said first mentioned means to filter operates upon pixel signals in a serial sample as a low-pass filter having an output which is the sum of a factor of the pixel signal input of the current sample plus a factor of the pixel signal filter output of the pixel preceding the current sample; and including a high-pass filter operating upon pixel signals in a serial sample having a memory containing a second look-up table which issues a high-pass filter value for all values of pixel signals in the serial sample and all values of the low-pass filter signal value which is the difference between a function of the value of the current pixel signal sample and a function of the low pass filtered signal value for the preceding pixel signal.

7. An image analysis system according to claim 6 for two dimensional filtering of an array of pixel signals derived from said image including means to repetitively operate said means to sample said pixel signals serially to provide a plurality of signal series representing the magnitude of light received from respective corresponding discrete areas along a plurality of adjacent bands of discrete areas on an object producing said image; means to identify each pixel signal in a series; second means to filter operating upon corresponding pixel signals in successive serial samples identified by said means to identify as a second low-pass filter having a memory containing a low-pass filter look-up table producing an output which is the sum of a factor of the pixel signal input of the current sample plus a factor of the pixel signal filter output of the current sample pixel for the preceding series of pixel signal samples; and a high-pass filter operating upon corresponding pixel signals in successive serial samples identified by said means to identify having a memory containing a high-pass filter look-up table producing a high-pass filter value for all values of the current sample pixel signal and all values of said second low-pass filter output signal value which is the difference between a function of the value of the current pixel signal sample and a function of the second low-pass filter output signal value for the current pixel signal for the preceding series of pixel signal values.

8. An image analysis system comprising a camera having a linear array of pixels each providing a signal representing the magnitude of light received from a corresponding discrete area along a band of discrete areas on an object producing said image, means to scan said linear array of pixels for successive adjacent bands of discrete areas on said object producing said image to produce serially a plurality of rows of pixels for said bands in which pixels are arranged in columns in adjacent bands; means to assign a column number to pixels in the same column; high pass row filter means to filter pixel-to-pixel signal intensities in rows; high pass column filter means to filter pixel-to-pixel intensities in columns; and means to vector combine signals as a function of said signals from said row filter means and from said column filter means in a memory having a value for every possible combination of the signals from said row and column filter means.

9. An image analysis system according to claim 8 wherein said row and column filters includes low pass filters.

10. An image analysis system comprising a camera having a linear array of pixels each providing a signal representing the magnitude of light received from a corresponding discrete area along a band of discrete areas on an object producing said image, means to scan said linear array of pixels for successive adjacent bands of discrete areas on said object producing said image to produce serially a plurality of rows of pixels for said bands in which pixels are arranged in columns in adjacent bands; means to assign a column number to pixels in the same column; row filter means to filter pixel-to-pixel signal intensities in rows; column filter means to filter pixel-to-pixel intensities in columns; and means to vector combine signals as a function of said signals from said row filter means and from said column filter means in a memory having a value for every possible combination of the signals from said row and column filter means wherein said means to combine signals includes a memory containing a look-up table; and a computer for loading said memory with said look-up table according to a selected function; and wherein said selected function is the square root of the sum of the squares of the values represented by the signals from said row filter means and said column filter means.

11. An image analysis system comprising a camera having a linear array of pixels each providing a signal representing the magnitude of light received from a corresponding discrete area along a band of discrete areas on an object producing said image, means to scan said linear array of pixels for successive adjacent bands of discrete areas on said object producing said image to produce serially a plurality of rows of pixels for said bands in which pixels are arranged in columns in adjacent bands; means to assign a column number to pixels in the same column; row filter means to filter pixel-to-pixel signal intensities in rows; column filter means to filter pixel-to-pixel intensities in columns; and means to vector combine signals as a function of said signals from said row filter means and from said column filter means in a memory having a value for every possible combination of the signals from said row and column filter means wherein said means to combine signals includes a memory containing a look-up table; and a computer for loading said memory with said look-up table according to a selected function; and wherein said selected function is the sum of the absolute values represented by the signals from said row filter means and said column filter means.

12. An image analysis system according to claim 11 wherein said selected function is a zero multiplier for one of the absolute values represented by the signals from said row filter means and said column filter means.

13. An image analysis system comprising a camera having a linear array of pixels each providing a signal representing the magnitude of light received from a corresponding discrete area along a band of discrete areas on an object producing said image, means to scan said linear array of pixels for successive adjacent bands of discrete areas on said object producing said image to produce serially a plurality of rows of pixels for said bands in which pixels are arranged in columns in adjacent bands; means to assign a column number to pixels in the same column; row filter means to filter pixel-to-pixel signal intensities in rows; column filter means to filter pixel-to-pixel intensities in columns; and means to vector combine signals as a function of said signals from said row filter means and from said column filter means in a memory having a value for every possible combination of the signals from said row and column filter means wherein said means to combine signals includes a memory containing a look-up table; and a computer for loading said memory with said look-up table according to a selected function; and wherein said computer loaded look-up table is in accordance with the equation:

$$V(r,c) = \text{a function of } R*F(R) \text{ and } S*F(C)$$

where
F(R) is the row filter signal value,
F(C) is the column filter signal value,
R and S are selected numbers comprising gains applied to the row and column filter outputs, and
V(r,c) is the vector combination signal value.

14. An image analysis system comprising a camera having a linear array of pixels each providing a signal representing the magnitude of light received from a corresponding discrete area along a band of discrete areas on an object producing said image, means to scan said linear array of pixels for successive adjacent bands of discrete areas on said object producing said image to produce serially a plurality of rows of pixels for said bands in which pixels are arranged in columns in adjacent bands; means to assign a column number to pixels in the same column; row filter means to filter pixel-to-pixel signal intensities in rows; column filter means to filter pixel-to-pixel intensities in columns; means to vector combine signals as a function of said signals from said row filter means and from said column filter means in a memory having a value for every possible combination of the signals from said row and column filter means; means to identify for each vector combine signal output the pixel signal row of said output and the pixel signal output in said identified row; a threshold memory; means to apply to said memory signals from said vector combine means and the identification of the pixel signal row and pixel signal count in said row of said signals from said vector combine means; and a look-up table in said threshold memory for issuing a characteristic event signal in response to a predetermined magnitude of said signal from said vector combine means and the identification of a predetermined pixel by row and count in said row as the source of said signal from said vector combine means.

15. An image analysis system according to claim 14 including means to group a selectable number of adjacent pixel signal rows; means to group a selectable number of adjacent pixel signal counts in said selected pixel signal rows; means to group grouped pixels into cells; means to set threshold values individual to said cells for predetermined magnitudes of said signals from said vector combine means; and wherein said look-up table in said memory issues a characteristic event signal in response to a signal from said vector combine means for a pixel when said signal exceeds the set threshold value for said cell containing said pixel.

16. An image analysis system comprising a camera having a linear array of pixels each providing a signal representing the magnitude of light received from a corresponding discrete area along a band of discrete areas on an object producing said image, means to scan said linear array of pixels for successive adjacent bands of discrete areas on said object producing said image to produce serially a plurality of rows of pixels for said bands in which pixels are arranged in columns in adjacent bands; means to assign a column number to pixels in the same column; row filter means to filter pixel-to-pixel signal intensities in rows; column filter means to filter pixel-to-pixel intensities in columns; means to vector combine signals as a function of said signals from said row filter means and from column filter means in a memory having a value for every possible combination of the signals from said row and column filter means; a stacked memory and means to apply signals from said vector-combine signal means to said stacked memory and to withdraw said signals from said stacked memory on a first-in-first-out basis.

17. An image analysis system according to claim 16 including means to identify pixels in a row, means to identify pixel rows; and wherein said means to apply signals to said stacked memory includes means to identify the source of said signal from said vector-combine signal means by pixel and row.

18. An image analysis system according to claim 16 including said means to apply signals to said stacked memory applies row identification only at the end of a row series of pixel signals.

19. An image analysis system according to claim 14 including a processor for characteristic event signals from said look-up table for characteristic event signals including means to group a selectable number of adjacent pixel signal rows; means to group a selectable number of adjacent pixel signal counts in said selected pixel signal rows; means to group grouped pixels and grouped pixel rows into cells; means to selectively set said processor to impose a predetermined process on said characteristic event signals for all pixels in said cells.

20. An image analysis system according to claim 19 wherein said predetermined process is the run-length encoding of a string of contiguous characteristic even signals.

21. An image analysis system according to claim 19 wherein said predetermined process is to inhibit the processing of characteristic event signals.

22. An image analysis system according to claim 19 wherein said predetermined process is to issue initializing signals to one of said filters.

23. An image analysis system according to claim 14 including a stacked memory and means to apply signals from said look-up table in said memory for issuing a characteristic event signal to said stacked memory and means to withdraw said signals from said stacked memory on a first-in-first out basis.

24. An image system according to claim 33 including means to identify pixels in a row; means to identify pixel rows; and wherein said means to apply signals to said stacked memory includes means to identify the source of said signal by pixel and row and the magnitude of said signal from said means to vector-combine signals.

25. An image system according to claim 24 wherein said means to apply signals to said stacked memory applies row identification only at the end of a row series of pixel signals for a row having a characteristic event signal.

26. A filter for digital signals comprising a series of discrete signals in a finite range of values comprising a memory; a first input for said memory for all possible values of the signal to be filtered; a memory output, a latch for retaining signals connected to the memory output, a latch output, a second input for said memory, said latch output being connected to said second memory input; means to establish a look-up table in said memory having an output in response to the current discrete input signal on said first input for said memory and an input signal from said latch on said second input to said memory of a discrete input signal preceding the current discrete input signal; a second memory; a first input for said second memory for all possible values of the signal to be filtered; a second input for said second memory for all possible signal values of said latch output; an output from said second memory; and means to establish a second look-up table in said second memory for issuing output signals on said output from said second memory in response to the current discrete input signal on said first input for said second memory and an input signal from said latch on said second input for said second memory.

27. A filter according to claim 26 wherein said means to establish said second look-up table in said second memory establishes a table according to the equation:

$$F(R) = L^*F(r,c) - M^*G(r,c-1)$$

where
- $F(r,c)$ is the current discrete input signal,
- $G(r,c-1)$ is the latch output, the first mentioned memory output for the discrete input signal next preceding the current discrete input signal,
- L and M are each a number, and
- $F(R)$ is the current second memory output.

28. A filter according to claim 27 to high-pass filter the signal wherein L and M are each one(1).

29. A filter for digital signals comprising a series of discrete signals in a finite range of values comprising a memory; a first input for said memory for all possible values of the signal to be filtered; a memory output, a latch for retaining signals connected to the memory output, a latch output, a second input for said memory, said latch output being connected to said second memory input; means to establish a look-up table in said memory having an output in response to the current discrete input signal on said first input for said memory and an input signal from said latch on said second input to said memory of a discrete input signal preceding the current discrete input signal; means to generate a plurality of successive series of discrete signals; wherein said means to establish a look-up table in said memory establishes a table according to the equation:

$$H(r,c) = K^*F(r,c) + (1-K)^*H(r-1,c),$$

where
- $F(r,c)$ is the current discrete input signal,
- $H(r-1,c)$ is the latch output for the signal in the next preceding series of signals which correspond to the current discrete signal input in its series,
- $H(r,c)$ is the current memory output, and
- K is a number between zero and one selected according to the desired time constant of the filter;
- a second memory, a first input for said second memory for all possible values of the signal to be filtered; a second input for said second memory for all possible signal values of said latch output; an output from said second memory; and means to establish a second look-up table in said second memory for issuing output signals on said output from said second memory in response to the current discrete input signal on said first input for said second memory and an input signal from said latch on said second input for said second memory.

30. A filter according to claim 29 wherein said second look-up table in said second memory establishes a table according to the equation:

$$F(C) = P^*F(r,c) - Q^*H(r-1c)$$

where
- $F(r,c)$ is the current discrete input signal,
- $H(r-1,c)$ is the latch output for the signal in the next preceding series of signals which corresponds to the current discrete signal input in its series,
- $F(C)$ is the current second memory output, and
- P & Q are each a number.

* * * * *